United States Patent [19]

Lang et al.

[11] Patent Number: 4,938,950
[45] Date of Patent: Jul. 3, 1990

[54] COSMETIC COMPOSITION BASED UPON CHITOSAN AND AMPHOLYTIC COPOLYMERIZATES, AS WELL AS NEW CHITOSAN/POLYAMPHOLYTE SALTS

[75] Inventors: Guenther Lang, Reinheim; Harald Wendel, Ober-Ramstadt, both of Fed. Rep. of Germany

[73] Assignee: Wella Aktiengesellschaft, Darmstadt, Fed. Rep. of Germany

[21] Appl. No.: 136,857

[22] Filed: Dec. 22, 1987

[30] Foreign Application Priority Data

Dec. 23, 1986 [DE] Fed. Rep. of Germany ....... 3644097

[51] Int. Cl.$^5$ .................... A61K 7/06; A61K 7/09; C08B 37/08
[52] U.S. Cl. .................... 424/47; 424/63; 424/70; 8/405; 8/406; 536/20; 514/55; 514/880; 514/844
[58] Field of Search .................... 514/55, 880, 844; 536/20; 424/63, 70, 47, 72; 8/405, 406

[56] References Cited

U.S. PATENT DOCUMENTS

| | | | |
|---|---|---|---|
| 3,632,754 | 1/1972 | Balassa | 424/95 |
| 3,879,376 | 4/1975 | Vanlerberghe et al. | 514/846 |
| 3,953,608 | 4/1976 | Vanlerberghe et al. | 514/777 |
| 4,031,025 | 6/1977 | Vanlerberghe et al. | 514/777 |
| 4,202,881 | 5/1980 | Gross et al. | 424/70 |
| 4,271,058 | 6/1981 | Trabitzsch et al. | 524/253 |
| 4,373,096 | 2/1983 | Koshugi | 536/20 |
| 4,528,283 | 7/1985 | Lang et al. | 514/55 |
| 4,603,048 | 7/1986 | Konrad et al. | 424/70 |
| 4,664,806 | 5/1987 | Merz | 536/4.1 |
| 4,711,776 | 12/1987 | Suzuki et al. | 424/70 |
| 4,772,689 | 9/1988 | Lang et al. | 536/20 |
| 4,772,690 | 9/1988 | Lang et al. | 536/20 |
| 4,822,598 | 4/1989 | Lang et al. | 536/20 |
| 4,835,266 | 5/1989 | Lang et al. | 536/20 |

FOREIGN PATENT DOCUMENTS

| | | |
|---|---|---|
| 58-116409 | 7/1983 | Japan . |
| 61-34004 | 2/1986 | Japan . |
| 2104091 | 3/1983 | United Kingdom . |

OTHER PUBLICATIONS

Muzzarelli et al; Carb. Res. 107:199-214 (1982).

Primary Examiner—Ronald W. Griffin
Assistant Examiner—Nancy S. Carson
Attorney, Agent, or Firm—Michael J. Striker

[57] ABSTRACT

A cosmetic composition is disclosed for the treatment of hair or skin, based upon 0.05 to 10% by weight of chitosan, and characterized by a content of 0.05 to 20% by weight of an ampholytic copolymerizate of formula (I)

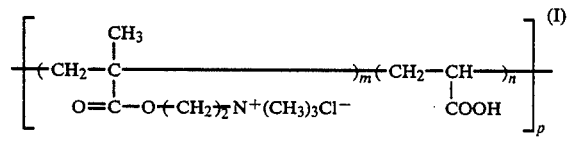

wherein $m=0.5$ to 0.9, $n=0.1$ to 0.5, $m+n=1$ and p being such that the ampholytic copolymerizate has a molecular weight of from 1,000 to 3,000,000.

wherein $m=0.1$ to 0.9 and $n=0.5$ to 0.9. The composition provides clear, smooth films, which are neither sticky in moist climate, nor brittle in dry climate. Also disclosed are new chitosan/polyampholyte salts, obtained by reaction of chitosan with an ampholytic copolymerizate of formula (I).

10 Claims, No Drawings

COSMETIC COMPOSITION BASED UPON CHITOSAN AND AMPHOLYTIC COPOLYMERIZATES, AS WELL AS NEW CHITOSAN/POLYAMPHOLYTE SALTS

BACKGROUND OF THE INVENTION

The invention concerns a cosmetic composition based upon aqueous chitosan/polyampholyte mixtures or water-soluble chitosan/polyampholyte salts, which are obtained by combination of chitosan with determined ampholytic copolymerizates.

Chitosan is a polyglucosamine produceable by means of deacetylation of chitin. It has already been suggested for employment in numerous cosmetic compositions. Therewith, the chitosan is employed in particular in the form of its water-soluble salts with organic acids or anion tensides. In this connection, reference is made to European Patent No. 0 002 506, German Patent No. 26 27 419, as well as German laid-open application No. 31 40 134.

The previously employed chitosan salts, however, tend to form turbid, brittle and only slightly adhering films, on account of their strong ionic, salt-like character. For this reason, fixers containing the high content of these chitosan salts necessary for a strong fixing ability, display a cosmetically unsatisfactory, strong scaling-off of the chitosan salt film from the hair, whereby a fixing of difficult to fix hair is not possible in this manner. Moreover, it is known that salts of chitosan with multivalent anions, such as for example sulfates or phosphates, are insoluble or only slightly soluble in water. Even with polyanions, such as for example polyacrylic acid or alginic acid, chitosan forms polysalts that are insoluble in water.

SUMMARY OF THE INVENTION

It is therefore an object according to the present invention to make available a cosmetic composition based upon chitosan, with which the above described disadvantages regarding film-forming characteristics and solubility can be provided.

It has surprisingly been discovered, that salts of chitosan with determined ampholytic copolymerizates, the latter known from British laid-open application No. 2 104 091 as well as U.S. Pat. No. 4,271,058, are water-soluble, or the chitosan can be dissolved in aqueous solutions of these polyampholytes. By means of the combination of both these compounds, in other respects, the advantageous film-forming characteristics of a known synthetic polymer are bound with the known chitosan salts, without taking over the disadvantages of each starting material. (Reference is made to Example 2, infra.)

The subject of the present invention is therefore a cosmetic composition for the treatment of hair and/or skin, based upon 0.05 to 10% by weight of chitosan, which is characterized by a content of 0.05 to 20% by weight of an ampholytic copolymerizate of formula (I) wherein m=0.5 to 0.9, n=0.1 to 0.5, m+n=1 and p being such that the ampholytic copolymerizate has a molecular weight of from 1,000 to 3,000,000.

The ampholytic copolymerizate of formula (I) (also referred to as "polyampholyte" herein,) as well as processes for its production, are described in laid-open British application for patent No. 2 104 091, as well as in U.S. Pat. No. 4,271,058. The polyampholytes of formula (I), suitable for employment in the cosmetic compositions according to the present invention, possess a cationic portion of 50 to 90 mol-%, and a limit viscosity number (determined with a DIN-Ubbelohde capillary viscosimeter at 25° C. in an aqueous solution of 0.2 mol/l acetic acid and 0.1 mol/l sodium chloride) from 3.3 to 7.4 (ml/g).

The amphoteric copolymerizate of formula (I) may be obtained by copolymerizing acrylic acid with dimethyl aminoethyl methacrylate quaterized with methyl chloride. Those amphoteric copolymerizates can be produced by well known methods. In the copolymerization, water is generally used as a solvent and potassium peroxodisulfate, potassium peroxodisulfate/sodium hydrogen sulfite or hydrogen peroxide/$Fe^{+2}$ may be used as initiator. The resulting copolymerization may be used as such of after the purification. The purification is effected by dialysis or reprecipitation method.

The amphoteric copolymerizate comprises cationic monomer units of formula (a) and anionic monomer units of formula (b) randomly arranged in a molar ration of 50–90:50–10, preferably 70–80:30–20, to form a linear polymer having a molecular weight from 1,000 to 3,000,000.

This amphoteric copolymerizate is produced by polymerizing a mixture of the above-mentioned anionic monomer (b) and cationic monomer (a) in a given ratio in the presence of a polymerization initiator in water generally under a nitrogen stream. The polymerization is carried out generally at a temperature ranging from room temperature to 90° C. for 2 to 24 hours to obtain the intended copolymerizate having a molecular weight of preferably 3,000 to 1,000,000. Ether solution polymerization or bulk polymerization method may also be employed.

As an example of a synthesis of an ampholytic copolymerizate according to British Patent Application A No. 2,104,091 the following is provided (Example 2 of GB A No. 2,104,091): 600 g of ion-exchanged water, 103.8 g (0.5 mol) of dimethyl aminoethyl methacrylate quaterized with methyl chloride, 36 g (0.50 mol) of acrylic acid and 0.3 g of potassium peroxodisulfate were charged in a 1 l flask provided with a stirrer, a thermometer, a reflux condenser and a nitrogen gas inlet. The polymerization reaction was performed at 70° C. under a nitrogen stream for 6 hours. Then, the reaction mixture was cooled to room temperature and poured into 3000 g of acetone. An ampholytic copolymerizate thus precipitated was filtered.

The ratio of the contents of cationic monomer units (a) and anionic monomer units (b) determines the characteristics of the ampholytic copolymerizate.

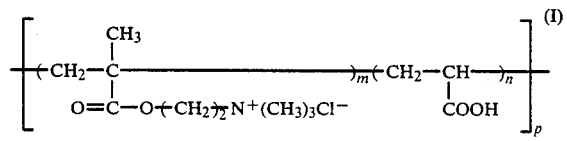

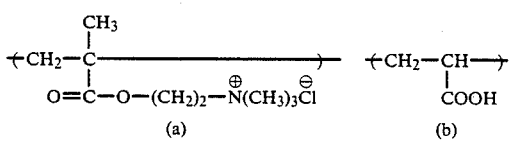

This is of particular significance for the solubility of the chitosan in aqueous solutions of the polyampholyte, or the water solubility of the formed chitosan/polyampholyte salts. The solubility of the chitosan in aqueous solutions of the polyampholyte increases, namely, with increasing cationic portions of the polyampholyte (see, e.g. Example 1).

Particularly advantageous are such chitosan/polyampholyte mixtures in which a polyampholyte having a limit viscosity number from 4.6 to 5.9 (determined in an aqueous solution of 0.2 mol/l acetic acid and 0.1 mol/l sodium chloride) as well as a content of cationic monomer units (a) from 70 to 80 mol-% and a content of anionic monomer units (b) from 20 to 30 mol-% is employed.

The molar ratio of chitosan (relative to its content of free amino groups) to ampholytic copolymerizate (relative to its anionic portion) should preferably amount to between 1:1 and 1:5 in the cosmetic composition according to the present invention.

The composition according to the invention, containing a chitosan/polyampholyte mixture or a chitosan/polyampholyte salt, is generally suitable for treatment of the hair or the skin. It can be provided, in particular, as a hair wash and/or body wash, toning shampoo, hairdo cream, hairdo lotion, hair dryer lotion, hairdo fixing agent, washing lotion, hair treatment, hair coloring agents, preparation for application before or after hair coloring, and as cosmetic agents for the care, protection or cleaning of the skin. Examples of cosmetic compositions for the care, protection or cleaning of the skin include astringents, foam bath and douche bath preparations, moisture-retaining creams, cold creams, body lotions, sun protection agents, and also make-up preparations such as make-up-removing milk products.

The chitosan and the ampholytic copolymerizate of the formula (I) are contained in the cosmetic compositions according to the present invention in a total amount from about 0.1 up to 30% by weight, preferably from 0.1 to 10% by weight.

The cosmetic compositions according to the present invention can contain, in addition to the content of chitosan and ampholytic copolymerizate, for the production of a cosmetic base, any of those components which are customarily employed in hair and skin treatment compositions, particularly anionic, cationic, amphoteric, zwitterionic or non-ionogenic surface-active tensides, foam synergists, stabilizers, sequestrants, pigments, thickeners, emulsifiers, buffers, preservatives, dyes, perfume oils, known cosmetic polymers such as anionic, non-ionic, cationic or amphoteric polymers, natural substances, cosmetic oils, fatty alcohols, waxes, foam stabilizers, anti-dandruff substances, reducing agents and propellant gases.

The cosmetic composition according to the present invention preferably displays a pH-value from 2 to 11, and can be provided in the form of an aqueous or aqueous-alcoholic preparation, particularly as a solution, a cream, a gel, as a dispersion or as an emulsion.

It is likewise possible to employ these compositions with the aid of an atomizer or other suitable spray apparatus, or in mixture with customary propellant agents liquefied under pressure as an aerosol spray (for example, an aerosol hair spray) or an aerosol foam from a pressure container.

In preferred manner, the cosmetic compositions according to the present invention involve compositions for the fixing of hairdos, such as for example, a liquid hair fixer or hair spray. Such compositions are customarily provided as aqueous or aqueous-alcoholic solutions, which are characterized by a content of a chitosan/polyampholyte mixture or a chitosan/polyampholyte salt. The chitosan/polyampholyte mixture or chitosan/polyampholyte salt can be employed itself as a film-forming or fixing resin; however, the hair fixing composition according to the present invention can also contain other film-forming natural or synthetic cosmetic polymers. Coming into consideration as natural polymers are, for example, shellac, alginate, gelatin, pectin and cellulose derivatives. Useful synthetic polymers include, for example, polyvinyl pyrrolidone, polyvinyl acetate, polyacrylic compounds such as e.g. acrylic acid- or methacrylic acid polymerizates, basic polymerizates of esters of acrylic acid or methacrylic acid with aminoalcohols or the salts or quaternization products of these basic polymerizates, polyacrylonitrile, as well as co- or terpolymerizates of these compounds, for example, polyvinyl pyrrolidone-vinyl acetate.

The composition then displays, in particular, a pH-value between 6 and 8. Such a composition for the fixing of hairdos customarily contains the film-forming polymers in a total amount from about 0.1 to 6.0% by weight. When the composition contains still other film-forming polymers, in addition to the present chitosan/polyampholyte mixture or chitosan/polyampholyte salt, then the content of the chitosan/polyampholyte mixture or chitosan/polyampholyte salt is reduced correspondingly.

Examples of alcohols coming into consideration for cosmetic purposes include, in particular, the customarily employed lower alcohols with 1 to 4 carbon atoms, such as e.g. ethanol and isopropanol.

When the composition for the fixing of hairdos is provided in the form of an aerosol preparation, which is sprayed from a pressure container, then the cosmetic base contains about 10 to 60% by weight of a propellant or blowing agent, Examples of propellants which can be employed are chlorofluoroalkanes, such as e.g. $CCl_3F$, $CCl_2F_2$, $C_2Cl_3F_3$, $(CCl_2F)_2$, $CHCl_2F$ and $(CClF_2)_2$, easily volatile hydrocarbons, such as e.g. n-butane and n-propane, or even dimethylether, carbon dioxide, dinitrogen monoxide, nitrogen, methylene chloride and 1,1,1-trichloroethane.

The composition according to the present invention for the fixing of hairdos can contain, moreover, the additives customary for such compositions, such as for example, perfume oil, bactericides, fungicides, combability-improving substances, modifying agents, such as e.g. silicon oil, and softeners, such as e.g. isopropyl myristate, phthalic acid diethylester and diethyl stearate.

The composition according to the present invention for the fixing of hairdos can, if necessary, simultaneously color or tone the hair, by means of a content of cosmetic dyes. Such preparations are commercially known, among other names, as coloring hair fixers or toning hair fixers. They contain, additionally, directly-on-the-hair-drawing cosmetic dyes known to be customary for hair fixers, such as for example, aromatic nitro-dyes (e.g. 1,4-diamino-2-nitro-benzene, picramic acid, 1-hydroxy-2-amino-4-nitro-benzene and 1,4-bis-[(2-hydroxyethyl)-amino]-2-nitro-5-chloro-benzene), azo-dyes (e.g. C.I. 14 805—Acid Brown 4), anthraquinone dyes (e.g. C.I. 61 105—Disperse Violet 4) and triphenylmethane dyes (e.g. C.I. 42 535—Basic Violet 1), whereby the dyes of these classes, indeed according to the type of their substituents, can have acid, non-ionogenic or basic character. The total concentration of these dyes amounts to between about 0.01 and 2.0% by weight, customarily.

The composition according to the present invention for the fixing of hairdos displays, with equally good fixing of the hair compared to known and customary compositions based upon chitosan or chitosan salts, a particularly good combability and a good hold of the hair in wet condition, as well as a particularly acceptable hold of the hair in the dry state.

The present composition can also represent hair washing agents. It is then provided in the form of an aqueous solution or emulsion, and contains, in addition to about 0.5 to 6% by weight chitosan/polyampholyte mixture or chitosan/polyampholyte salt, at least one anionic, cationic, non-ionogenic or amphoteric tenside.

Such hair wash compositions generally contain the tenside(s) in a concentration between about 3 and 50% by weight, preferably 3 to 25% by weight. The pH-value is generally from about 3 to 9, preferably from 4 to 7.

The composition according to the present invention which is in the form of a hair wash usually further contains various additive substances, particularly perfumes, preservatives, thickeners, foam stabilizers, buffer substances, cosmetic resins, pigments or dyes.

Useful foam stabilizers would include, for example, the fatty amides, and particularly the mono- or diethanolamides of cocos fatty acids, lauryl- or oleic acid mono- or -diethanolamides, which are expediently provided in amounts from 1 to 10, prefereably from 1 to 3% by weight.

Under the designation thickeners, mention may be made by way of example of, particularly, acrylic polymers and cellulose derivatives, such as e.g. carboxymethylcellulose, hydroxypropylmethylcellulose and hydroxyethylcellulose. These thickeners are generally provided in amounts totalling from 0.1 to 5% by weight.

Tensides or surface-active agents, which can be used in combination with the new chitosan/polyampholyte mixtures or chitosan/polyampholyte salts, include, for example, the following:

(a) the anionic surface-active agents, such as for example, the alkali-, earth alkali-, ammonium- or alkanolamine salts of alkane sulfonates, alkyl sulfates and alkylether sulfates, the $C_{12}$–$C_{18}$-alkyl- and particularly $C_{12}$–$C_{14}$-alkyl-sulfatesodium salts or -triethanolamine salts, the sodium- or triethanolamine salts of lauryl- or tetradecylether sulfates, the disodium salts of the sulfosuccinic semiesters of alkanolamides, the soaps and the polyethercarboxylic acids;

(b) the non-ionic surface-active agents, such as for example, oxyethylated fatty alcohols with 12 to 18 carbon atoms, for example with up to 40 mol ethylene oxide per mol fatty alcohol, oxyethylated lauryl-, tetradecyl-, cetyl-, oleyl- and stearyl alcohols, alone or in mixture; the fatty alcohols of oxyethylated lanolin or oxyethylated lanolin; polyglycolethers of saturated or unsaturated fatty alcohols and alkylphenols with 8 to 30 carbon atoms in the alkyl group and 1 to 10 glyceryl units in the molecule; fatty acid alkanolamides, sorbitan fatty acid esters, as well as oxyethylated sorbitan fatty acid esters;

(c) the cationic surface-active agents, such as for example, the dilauryldimethylammonium chloride, the chloride or bromide of alkyldimethylbenzylammonium, the alkyltrimethylammonium salts, for example, cetyltrimethylammonium chloride or -bromide, the alkyldimethylhydroxyethylammonium chloride or -bromide, the dialkyldimethylammonium chloride or -bromide, alkyl pyridinium salts, for example, lauryl- or cetyl pyridinium chloride, the alkylamidethyltrimethylammonium ether sulfate, compounds with cationic character, such as aminoxides, for example, alkyldimethylaminoxide and alkylaminoethyldimethylaminoxide, oxyethylalkylammonium phosphate, pentaoxyethylammonium chloride or alkyldimethylammonium saccharinate;

(d) the amphoteric or zwitterionic surface-active agents, such as for example, the carboxyl derivatives of imidazole, the N-alkylbetaines, the N-alkylamidobetaines, the N-alkylsufobetaines, the N-alkylaminopropionates, the alkyldimethylammonium acetates, the $C_{12}$–$C_{18}$-alkyldimethylcarboxymethylammonium salts, as well as the fatty acid alkylamidobetaines, for example, dimethyl-carboxymethylene propylene amido-stearate-betaine.

The cosmetic compositions according to the present invention can also represent creams or lotions for employment as hair treatments or skin care compositions. They are then provided mainly in the form of an oil-in-water or water-in-oil emulsion or suspension and contain, in addition to the chitosan/polyampholyte mixture or the chitosan/polyampholyte salt, cationic, non-ionogenic, amphoteric or anionic emulsifiers, as well as any of the following as components of the oil phase: e.g. fatty alcohols, fatty acid esters or -amides, moreover, perfume oils, petrolatum, wool fatty alcohol or solid or liquid paraffin.

When the composition according to the present invention represents a hair coloring or hair toning composition it is likewise preferably provided in the form of a cream, a lotion or a shampoo, and additionally contains about 0.05 to 2.0% by weight of a customary, directly-on-the-hair-drawing dye from the group of the aromatic nitro-dyes, azo-dyes, anthraquinone days and triphenylmethane dyes, whereby the dyes of these classes, indeed depending upon the type of their substituents, can have acid, non-ionogenic or basic character. Moreover, these compositions can contain, if necessary, alkalization agents, antioxidants, as well as further cosmetic additives and adjuvants customary for such compositions.

As already mentioned above, the cosmetic composition according to the present invention can also be employed for the treatment of skin. For this purpose, it is preferably provided in the form of a cream, a gel, an emulsion or an aqueous or aqueous-alcoholic solution, which contains the chitosan/polyampholyte mixture or chitosan/polyampholyte salt in a concentration from about 0.1 to 10% by weight, and preferably from 0.2 to 6% by weight.

The additives generally contained in such cosmetic preparations include, for example, perfumes, dyes, preservatives, thickeners, sequestrants, emulsifiers, sun protection filters and the like.

These preparations for the treatment of skin are provided in particular in the form of a cream or lotion for care of the hands or the face, or in the form of a sun protection cream, a colored cream, a make-up-removing milk product, a foam bath or douche bath preparation, or even in the form of a deodorizing preparation.

Such preparations are produced by classical techniques. For example, in order to form a cream, one can emulsify an aqueous phase, which contains the chitosan/polyampholyte mixture or the chitosan/polyampholyte salt according to the present invention and, if necessary, other components or adjuvants, and an oily phase. For the oily phase, one can employ different types of compounds, for example, paraffin oil, vaseline oil, sweet almond oil, avocado oil, olive oil, fatty acid esters, such as for example, glyceryl monosterate, ethyl palmitate and isopropyl palmitate, or alkyl myristates, such as for example, propyl myristate, butyl myristate and cetyl myristate. One can also add to these fatty acid alcohols, for example, stearyl- or cetyl alcohol, or waxes, such as for example, beeswax or wool wax.

The chitosan/polyampholyte mixture or chitosan/polyampholyte salt can be contained in these cosmetic preparations for the care of skin not only as the main active substance, but also as an adjuvant.

The skin treatment compositions according to the present invention do not impair the natural cutaneous respiration, and facilitate a stabilization of the moisture content of the skin. Moreover, these compositions impart to the skin a soft feel and an outstanding pliancy.

The chitosan/polyampholyte mixture or chitosan/polyampholyte salt contained in the compositions according to the present invention are obtained by means of dissolving chitosan in an aqueous solution of an ampholytic copoymerizate of formula (I), or by means of reacting an aqueous solution of a water-soluble chitosan salt with an ampholytic copolymerizate of formula (I). The reaction can be performed not only at temperatures between about 20°–25° C., but also between about 40° to 60° C. The reaction period amounts to about 8 to 16 hours at temperatures from 20° to 25° C., and from 1 to 2 hours at temperatures from 40° to 60° C. If necessary, after conclusion of the reaction, water-insoluble components can be removed from the solution by means of filtration.

The amount of polyampholyte necessary for dissolving the chitosan, i.e. for the formation of the chitosan/polyampholyte salt, is dependent upon the magnitude of the anionic portion (n) of the polyampholyte, and can be calculated from the titrationally-determined acid group content of the polyampholyte. The molar ratio of chitosan (relative to its content of free amino groups) and polyampholyte (relative to its anionic portion) expediently amounts to from 1:1 to 1:5, whereby an equimolar ratio is preferred. There can, however, also be employed a slight deficiency or an optional excess of the polyampholyte.

Accordingly, the subject of the present invention also encompasses chitosan/polyampholyte salts, obtained by the above-described process.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

Production and Solubility of Chitosan/Polyampholyte Mixtures

An aqueous mixture, containing 1% by weight chitosan and the amount of a polyampholyte according to formula (I) theoretically necessary for the formation of a 1:1 salt of chitosan and polyampholyte, as set forth in Table 1, infra, is stirred overnight. Subsequently, the water-solubility of the formed chitosan/polyampholyte salt or the solubility of the chitosan in the polyampholyte solution, is determined.

EXAMPLE 2

Comparison Test

The aqueous chitosan/polyampholyte solutions, containing chitosan/polyampholyte salt, are purified by means of filtration and then dried at 30% relative air moisture on specially prepared glass plates for one week at room temperature (20° C.). Thereafter, the film quality is evaluated.

The characteristics of the relatively brittle, known chitosan salt films, and the sticky polymer films, are seen to be combined in advantageous manner. Solution C containing the chitosan/polyampholyte salt according to the present invention provides clear, smooth films, which are not sticky in moist climate (Comparison Example B) and, on the other hand, are not fragile and brittle in dry climate (Comparison Example A).

TABLE 1

| Cationic portion of the Polyampholyte (in mol %) | Limit Viscosity Number $\eta$ (ml/g)[1] | Content of Acid Groups[2] per gram Polyampholyte Solution (mmol H$^+$) | Dry Substance Content of Aqueous Polyampholyte Solution (% by weight)[3] | Necessary Amount Polyampholyte Solution per Gram Chitosan to form a 1:1 salt[4] (Gram) | Solubility of Chitosan in the Polyampholyte Solution |
|---|---|---|---|---|---|
| 0 | 14.3 | 5.82 | 40 | 1.07 | insoluble |
| 50 | 3.3 | 2.77 | 40 | 2.24 | limited solubility; strong milky turbidity |
| 70 | 4.6 | 1.71 | 41 | 3.62 | soluble w/ weak turbidity |
| 80 | 5.9 | 1.16 | 42 | 5.35 | soluble; clear w/ sl. residue |
| 90 | 7.4 | 0.62 | 42 | 10.02 | soluble; clear w/ |

TABLE 1-continued

| Cationic portion of the Polyampholyte (in mol %) | Limit Viscosity Number η (ml/g)[1] | Content of Acid Groups[2] per gram Polyampholyte Solution (mmol H+) | Dry Substance Content of Aqueous Polyampholyte Solution (% by weight)[3] | Necessary Amount Polyampholyte Solution per Gram Chitosan to form a 1:1 salt[4] (Gram) | Solubility of Chitosan in the Polyampholyte Solution |
|---|---|---|---|---|---|
| | | | | | sl. residue |

[1]The determination of the limit viscosity number η is done with a DIN-Ubbelohde-capillary viscosimeter in an aqueous solution of 0.2 mol/l acetic acid and 0.1 mol/l sodium chloride, at 25° C.
[2]The content of acid groups per gram of polyampholyte solution is determined by means of an acid-base titration with 0.1 n NaOH.
[3]The content of dry substance is calculated by means of a determination of the weight loss after two hours at 105° C.
[4]A chitin deacetylated to the extent of 90% (having 5.6 mmol free amino groups per gram chitosan) is employed as chitosan.

TABLE 2

| Comparison Example | A. | B. | C. |
|---|---|---|---|
| Solution (in water) of | 0.7% Chitosan and 1.8% Formic Acid (10%) | 2% Polyampholyte (with 70 mol-% cationic portion) | 0.48% Chitosan and 1.75% Polyampholyte (with 70 mol-% cationic portion) |
| Film Evaluation | turbid, milky, brittle film | clear, smooth, relativity soft film (sticky) | clear, smooth film |
| Pendulum Hardness According to Koenig[1] | | | |
| (a) at 30% relative moisture | 180 sec. | 61 sec. | 172 sec. |
| (b) at 70% relative moisture | 142 sec. | 2 sec. | 17 sec. |

[1]W. Koenig, "Hartemessungen mit dem Pendelharteprufer", Farbe und Lack 65, pages 435 to 443 (1959); German Industrial Norm DIN 53 157

EXAMPLE 3

Hair Fixer, Alcohol-free

| | |
|---|---|
| 0.70 g | Chitosan |
| 2.53 g | 41% aqueous solution of polyampholyte of formula (I) with a cationic portion of 70 mol % and a limit viscosity number of 4.6 (ml/g) |
| 0.75 g | Perfume oil |
| 0.10 g | Formaldehyde (25% aqueous solution) |
| 95.92 g | Water |
| 100.00 g | |

20 ml of this solution are distributed onto washed, hand towel-dried hair; the hair is set into a hairdo in customary manner; and dried. With good fixing effect, the hair displays, in comparison to use of a hair fixer based upon chitosan/formic acid, a more acceptable, elastic and softer hold.

EXAMPLE 4

Toning Hair Fixer

| | |
|---|---|
| 0.60 g | Chitosan |
| 15.03 g | 42% aqueous solution of polyampholyte of formula (I) with cationic portion of 90 mol % and a limit viscosity number of 7.4 (ml/g) |
| 0.05 g | Acid Brown 4 (C.I. 41 805) |
| 84.32 g | Water |
| 100.00 g | |

20 ml of this solution are distribued onto washed, hand towel-dried hair, and the hair is placed in customary manner and dried. Thereafter, the hair possesses a light red/brown coloration, and is fixed.

EXAMPLE 5

Hair Drier Lotion

| | |
|---|---|
| 0.240 g | Chitosan |
| 0.875 g | Polyampholyte solution from Example 3 |
| 35.000 g | Isopropanol |
| 0.500 g | Perfume |
| 0.100 g | Dye |
| 63.285 g | Water |
| 100.00 g | |

20 g of this solution are distributed onto washed, hand towel-dried hair. Thereafter, the hair is dried in customary manner. The hair displays an outstanding gliding quality upon brushing (i.e. "brushability") and is excellently conditioned with very good luster.

EXAMPLE 6

Hair Fixing Composition with Extra Strong Fixing

| | |
|---|---|
| 1.50 g | Chitosan |
| 15.03 g | Polyampholyte solution from Example 4 |
| 0.80 g | Perfume oil |
| 0.10 g | Formaldehyde (25% aqueous solution) |
| 82.57 g | Water |
| 100.00 g | |

20 ml of this solution are distributed onto washed, hand towel-dried hair. Subsequently, the hair is set into a hairdo in customary manner, and dried. With very strong fixing, the hair displays—in comparison to hair fixers based upon salts of chitosan with aliphatic organic acids—a more pleasant, more elastic and softer hold.

EXAMPLE 7

Hair Treatment Composition

| | |
|---|---|
| 0.30 g | Chitosan |
| 3.01 g | Polyampholyte solution from Example 4 |
| 3.00 g | Stearyl alcohol |
| 2.00 g | Tris-(oligooxyethyl)-octadecyl-ammonium phosphate |
| 1.00 g | Wool wax (*Adeps Lanae*) |
| 1.00 g | Petrolatum |
| 89.69 g | Water |
| 100.00 g | |

35 g of the hair treatment composition are distributed into washed hair and then, after a penetration period of 3 to 5 minutes, rinsed off with water. The result is an excellent hold, luster, as well as combability of the hair.

EXAMPLE 8

Hair Washing Composition

| | |
|---|---|
| 2.00 g | Chitosan |
| 9.52 g | Polyampholyte solution from Example 3 |
| 50.00 g | Dimethyl-carboxymethylene-propylene amido-stearate-betaine (30% aqueous solution) |
| 38.48 g | Water |
| 100.00 g | |

A clear shampoo is obtained. Hair washed therewith is excellently conditioned, with respect to luster, hold and combability.

EXAMPLE 9

Skin Cream

| | |
|---|---|
| 0.30 g | Chitosan |
| 3.00 g | Polyampholyte solution from Example 4 |
| 3.00 g | Stearyl alcohol |
| 1.00 g | Wool wax (*Adeps Lanae*) |
| 1.00 g | Petrolatum |
| 1.00 g | Sodium acetylstearyl sulfate |
| 90.70 g | Water, completely de-salted |
| 100.00 g | |

The cosmetic compositions according to Examples 3 to 9 are prepared as follows:

The chitosan is dissolved in the aqueous polyampholyte solution. Thereafter, the so-obtained chitosan/-polyampholyte solution is mixed with the others of components of the cosmetic composition (Examples 3, 4, 5, 6 and 8) or emulsuified (Examples 7 and 9).

The measurement of the limit viscosity numbers takes place in an aqueous solution of 0.2 mol/l acetic acid and 0.1 mol/l sodium chloride at 25° C., using a DIN-Ubbelohde-capillary viscosimeter.

All percentages set forth in this specification are percentages by weight, unless otherwise specified.

It will be understood that each of the elements described above, or two or more together, may also find a useful application in other types of compositions differing from the types described above.

While the invention has been illustrated and described as embodied in a cosmetic composition based upon chitosan and ampholytic copolymerizates, as well as new chitosan/polyampholyte salts, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Aqueous or aqueous-alcoholic cosmetic composition for treatment of hair or skin, comprising 0.05 to 10% by weight of chitosan, and 0.05 to 20% by weight of an ampholytic copolymerizate for formula (I)

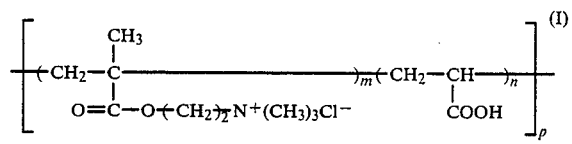

wherein m=0.5 to 0.9, n=0.1 to 0.5, m+n=1 and p being such that the ampholytic copolymerizate has a molecular weight of from 1,000 to 3,000,000.

2. The composition according to claim 1, containing said chitosan and said ampholytic copolymerizate of formula (I) in a total amount of 0.1 to 10% by weight.

3. The composition according to claim 1, wherein the molar ratio of chitosan, relative to its content of free amino groups, to ampholytic copolymerizate, relative to its anionic portion, amounts to between 1:1 and 1:5.

4. The composition according to claim 1, as a solution, cream, gel, dispersion or emulsion.

5. The composition according to claim 1, having a pH-value from between 2 to 11.

6. The composition according to claim 1, further comprising at least one cosmetic dye in a concentration from 0.01 to 2.0% by weight, said composition being in the form of a coloring hair fixer or a toning hair fixer.

7. The composition according to claim 1, further comprising at least one cationic, anionic, non-ionogenic or amphoteric tenside, said composition being in the form of a hair wash.

8. The composition according to claim 7, containing said tenside in an amount from 3 to 50% by weight and having a pH-value between 3 and 9.

9. The composition according to claim 1, containing as cosmetic base an aqueous or aqueous-alcoholic preparation, said composition being mixed with a propellant which is liquefied under pressure, filled into a pressure container and provided in the form of an aerosol spray or aerosol foam.

10. Chitosan/polyampholyte salt, obtained by reaction of chitosan or a water-soluble salt thereof with an equimolar amount of an aqueous solution of an ampholytic copolymerizate of formula (I)

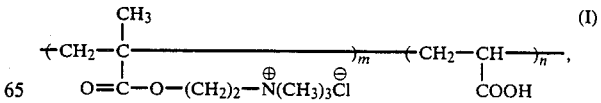

wherein m=0.5 to 0.9 and n=0.1 to 0.5.

* * * * *